(12) United States Patent
Canedy

(10) Patent No.: US 6,231,577 B1
(45) Date of Patent: May 15, 2001

(54) DEVICE FOR CREATING CYLINDRICAL BONE PLUGS FOR PATELLA-PATELLAR TENDON-TIBIA GRAFTS

(76) Inventor: James T. Canedy, 448 S. 82nd St., Omaha, NE (US) 68114

( * ) Notice: Subject to any disclaimer, the term of this patent is extended or adjusted under 35 U.S.C. 154(b) by 0 days.

(21) Appl. No.: 09/373,173

(22) Filed: Aug. 12, 1999

(51) Int. Cl.⁷ .................................................. A61B 17/14
(52) U.S. Cl. .............................. 606/79; 606/82; 409/138
(58) Field of Search .................. 606/79, 80, 81, 606/82, 83, 84, 85, 86, 167, 170, 171, 174; 409/73, 75, 138

(56) References Cited

U.S. PATENT DOCUMENTS

| | | | |
|---|---|---|---|
| 3,834,274 | * 9/1974 | Dowd | 409/138 |
| 3,992,734 | * 11/1976 | Chiron et al. | 452/156 |
| 4,222,692 | * 9/1980 | Pavlovsky | 409/141 |
| 4,416,278 | * 11/1983 | Miller | 606/174 |
| 5,540,692 | * 7/1996 | Tidwell | 606/79 |
| 5,616,146 | * 4/1997 | Murray | 606/80 |
| 5,693,056 | * 12/1997 | Carls et al. | 606/86 |
| 5,772,664 | * 6/1998 | DeSatnick et al. | 606/80 |
| 5,843,110 | * 12/1998 | Dross et al. | 606/171 |
| 5,928,238 | * 7/1999 | Scarborough et al. | 606/79 |

* cited by examiner

*Primary Examiner*—Gene Mancene
*Assistant Examiner*—Michael B. Priddy
(74) *Attorney, Agent, or Firm*—Zarley, McKee, Thomte, Voorhees & Sease; Dennis L. Thomte

(57) ABSTRACT

A bone cutter is provided for creating cylindrical bone plugs for patella-patellar tendon-tibia grafts and comprises a support having a pair of bone cutting wheels mounted thereon about a vertical axis. Each of the cutting wheels have an hourglass shape to define a circular opening therebetween. An adjustable plug guide is provided forwardly of the cutting wheels for guiding the harvested bone plug into proper engagement and alignment with the rotating cutting wheels.

11 Claims, 4 Drawing Sheets

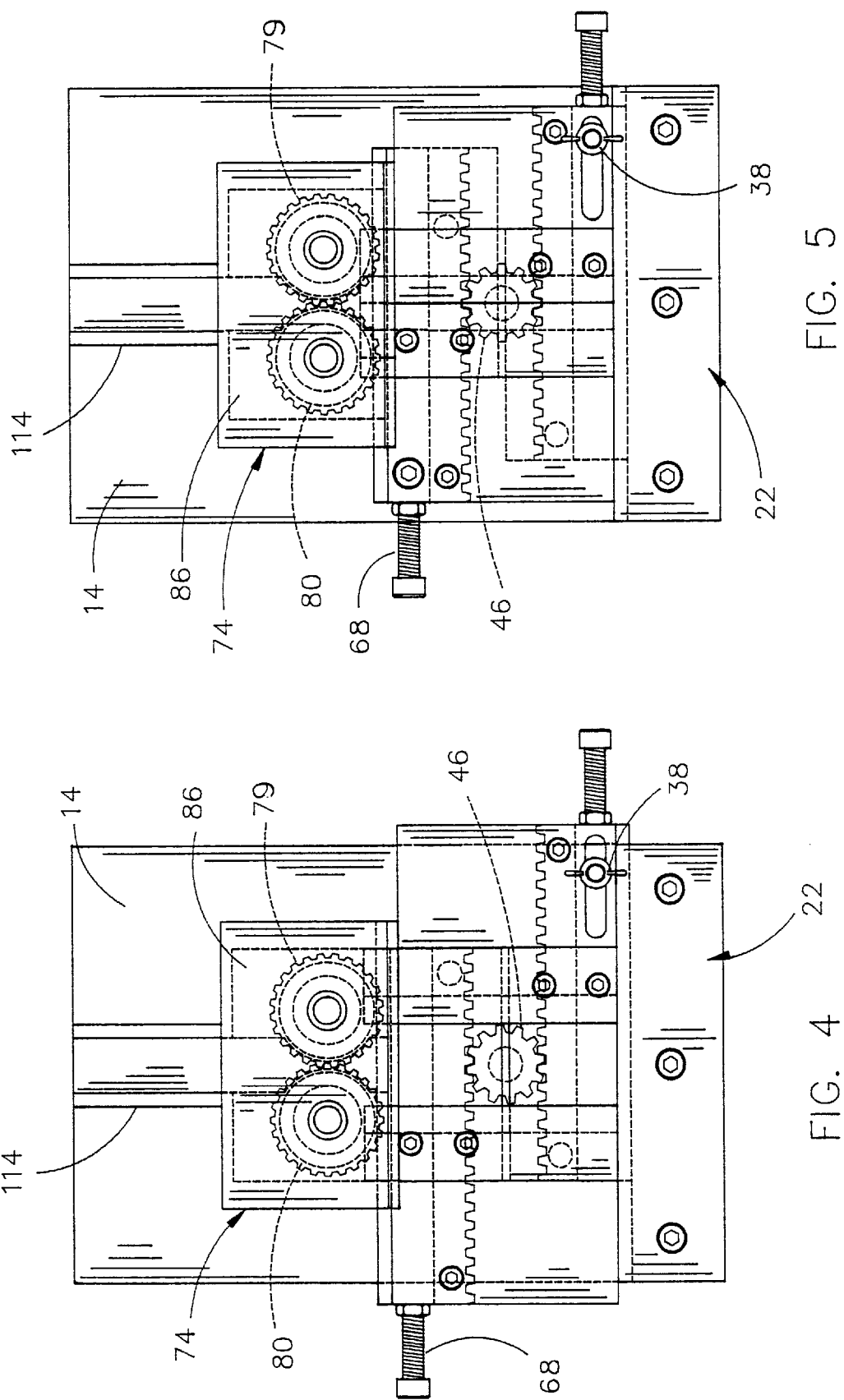

DEVICE FOR CREATING CYLINDRICAL BONE PLUGS FOR PATELLA-PATELLAR TENDON-TIBIA GRAFTS

BACKGROUND OF THE INVENTION

1. Field of the Invention

This invention relates to a bone cutting device and more particularly to a bone cutting device for creating cylindrical bone plugs for patella-patellar tendon-tibia grafts from bone plugs having other than a cylindrical shape.

2. Description of the Related Art

It has become standard procedure to use autologous patella-patellar tendon-tibia graft originating from the central one-third of the patellar tendon for anterior cruciate ligament (ACL) repair. The bone plugs of this autograft provide efficient healing with the osseous tunnels. Several studies have shown the cylindrical bone plug configuration to be superior to other geometric configurations. A cylindrical configuration provides a tighter fit in the tunnel and increases pull out strength.

As with any surgical procedure, ACL repair faces the concern of operation and anesthesia time. Increased length of operation has been associated with increased bacterial contamination of surgical wound, increased in-hospital mortality, increased post-op observation time, increased risk of hypothermia, short-term decline in Activities of Daily Living, post-op pulmonary complication, increased pain and fatigue, and increased risk for cardiovascular complications. Thus, a decrease in operative time would lead to less complications for the patient. A decrease in operative time would also decrease surgeon fatigue, which would directly increase the concentration of the surgeon towards the procedure.

Two methods have been previously demonstrated as ways to create cylindrical bone plugs on patellar tendon grafts. One of these methods involves the use of a circular oscillating saw to procure cylindrical bone plugs directly from the patient's knee. This technique provides reproducible plugs that are sized and shaped appropriately for the corresponding osseous tunnels. However, this particular saw has been described as cumbersome in the operating room, and there is a risk, although small, of thermal injury to the patient's skin from the heat produced by the body of the saw. Currently, this saw is not used in many institutions due to those reasons. In at least some institutions, grafts are harvested via a pneumatic saw, oscillating bone saw, or an osteotome and mallet. The harvested square grafts are then fashioned into cylindrical bone plugs with a Ronguer. The use of a Ronguer to shape a cylindrical bone plug from a square plug consumes considerable operative time and the plugs are not a standard, reproducible shape; however, this has become the commonly accepted method of shaping previously harvested patella-patellar tendon-tibia autograft bone plugs.

SUMMARY OF THE INVENTION

A device is described for creating cylindrical bone plugs for patella tendon-tibia grafts comprising a support having a bone cutting mechanism positioned thereon for grinding bone plugs, having other than a cylindrical shape, to create cylindrical bone plugs. The bone cutting mechanism comprises a pair of horizontally spaced, vertically disposed rotatable cutting wheels or cylinders which are rotated about a vertical axis. Each of the cutting wheels or cylinders have an hourglass configuration to define a substantially cylindrical space therebetween. A guide apparatus is provided on the support for guiding the bone plugs into the rotating cutting wheels or cylinders. The guide means is adjustable to accommodate various sizes of bone plugs. One of the cutting wheels is power driven with the other cutting wheel being driven by the power driven wheel through the use of meshing gears operatively connected to each of the cutting wheels.

It is therefore a principal object of the invention to provide an improved device for creating cylindrical bone plugs for patella tendon-tibia grafts.

Yet another object of the invention is to provide a device of the type described which provides reproducible shapes.

Still another object of the invention is to provide a device of the type described above including an adjustable bone plug guiding means so that the bone plugs are properly guided into contact with the rotating cutting wheels.

Yet another object of the invention is to provide a device of the type described above wherein the components thereof may be replaced as necessary.

Still another object of the invention is to provide a device of the type described above which is economical of manufacture and convenient to use.

These and other objects of the invention will be apparent to those skilled in the art.

BRIEF DESCRIPTION OF THE DRAWINGS

FIG. 4 is a top elevational view of the device of this invention;

FIG. 5 is a view similar to FIG. 4, but which illustrates the bone plug guidance means having been adjusted from that of FIG. 4;

DESCRIPTION OF THE PREFERRED EMBODIMENT

Figure 1:
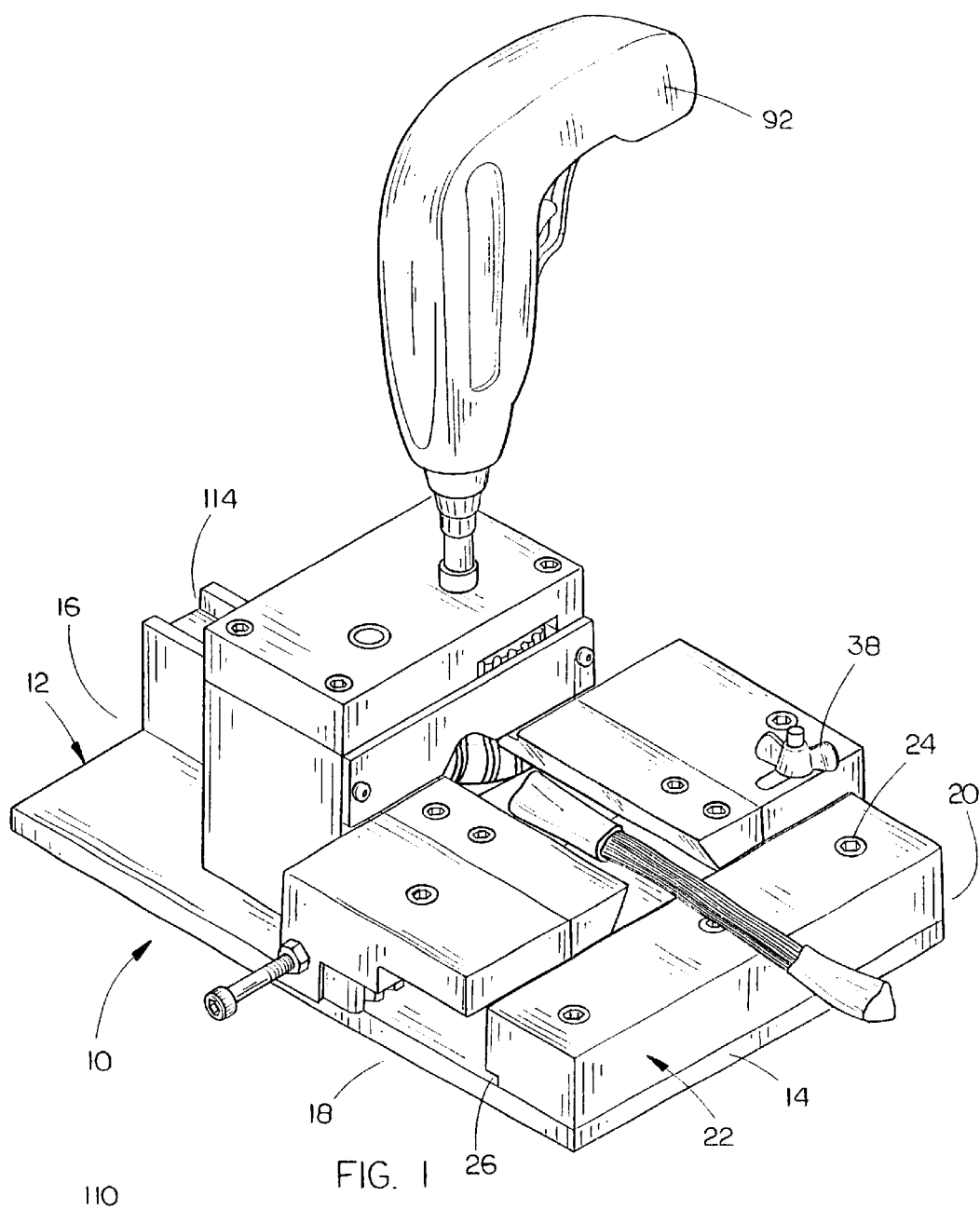
FIG. 1 is a perspective view of the bone cutting device of this invention.

The bone cutting device of this invention is referred to generally by the reference numeral 10 and includes a support plate 12. Although support plate 12 is shown to be a component of the invention, it is possible that the remaining components of the invention could be installed on a table top, counter top, or other suitable support. For purposes of description, support 12 will be described as having a forward end 14, rearward end 16, and opposite sides 18 and 20.

An elongated block member 22 is secured to the forward end of support 12 on the upper surface thereof by means of screws 24. As seen in FIG. 1, the rearward end of block member 22 is provided with a recessed area 26 formed in the lower end thereof.

Figure 3:
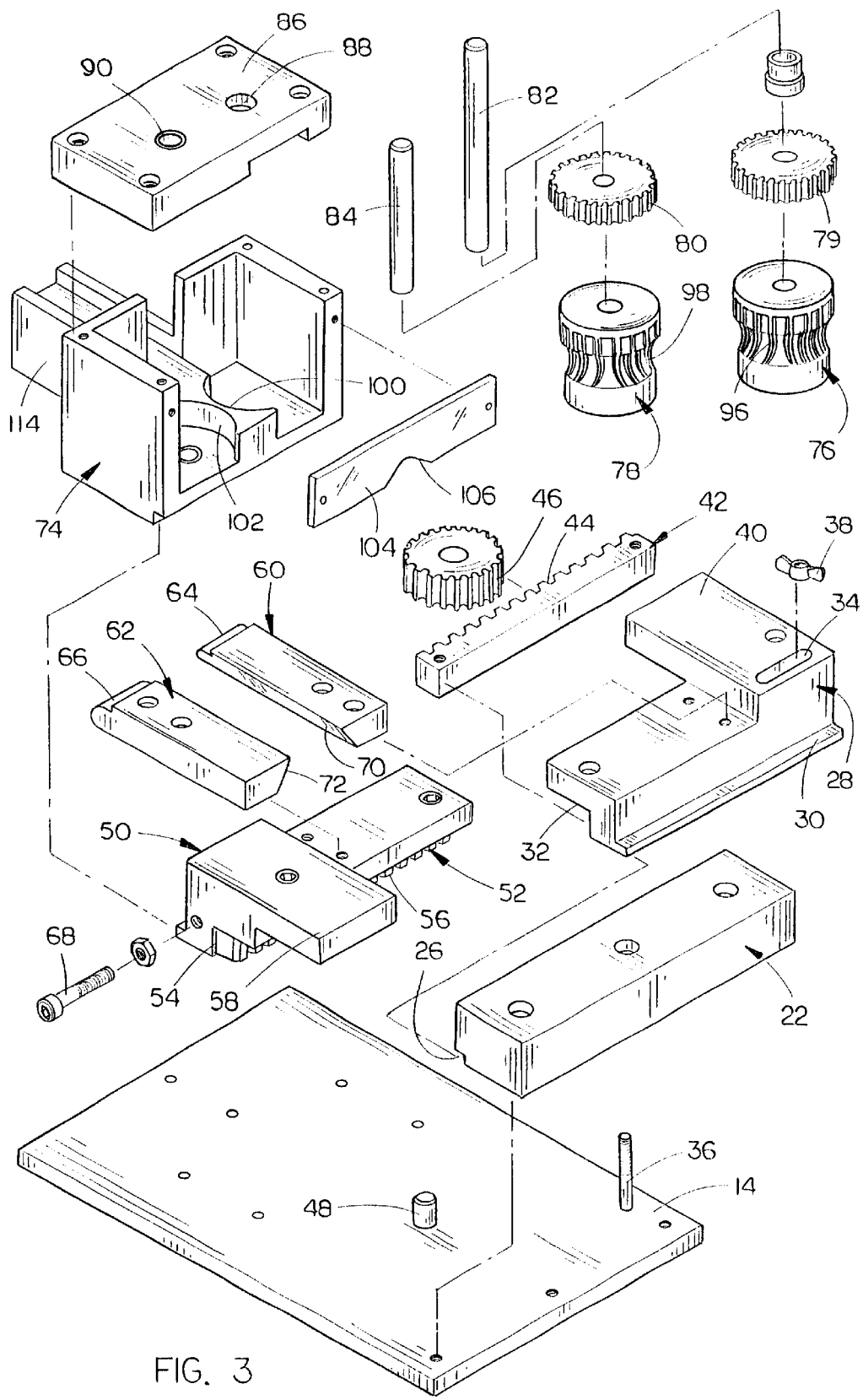
FIG. 3 is an exploded perspective view of the bone cutting device of this invention.
Figure 6:
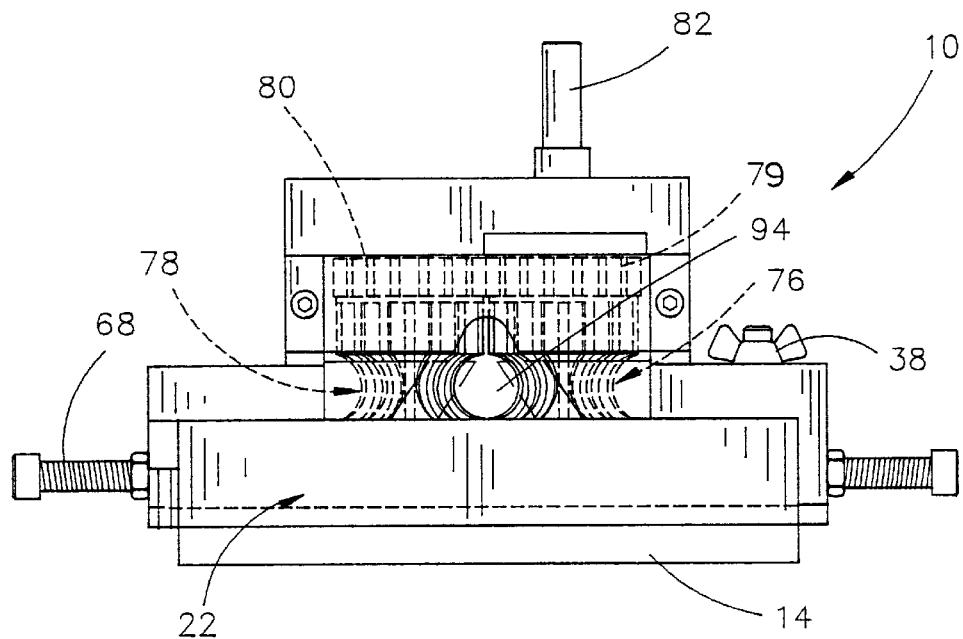
FIG. 6 is a front elevational view of the invention.
Figure 7:
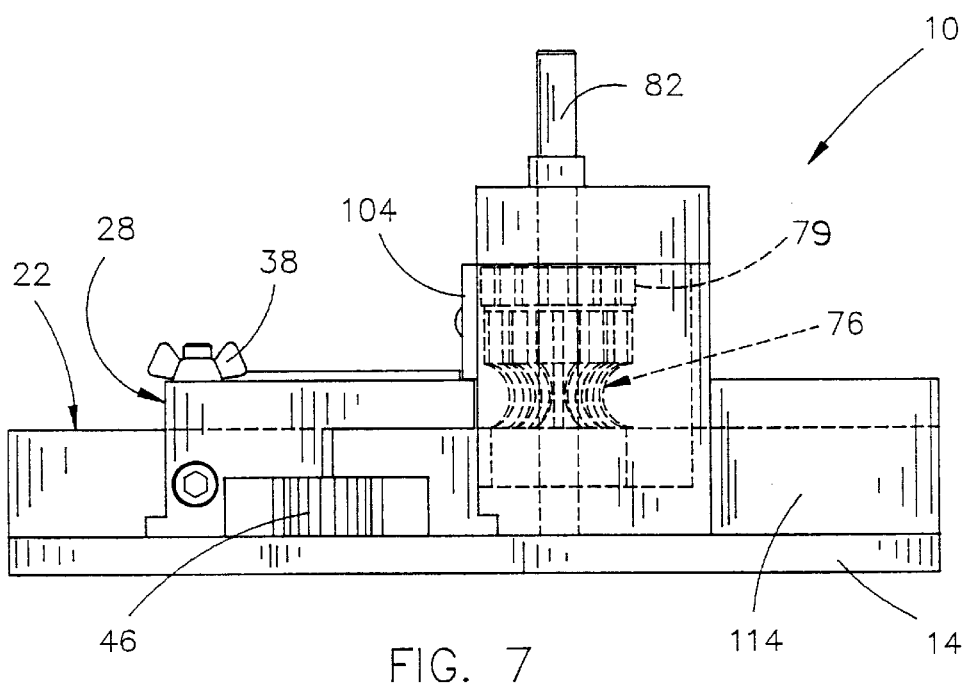
FIG. 7 is a side elevational view of the invention.

Slide member 28 is slidably positioned at the rearward end of block member 22 and has a lip or flange 30 slidably received in the recessed area 26 of block member 22. Slide member 28 is also provided with a recessed area 32 formed therein at its lower rearward end. Slide member 28 also has an elongated slot 34 extending downwardly therethrough which adjustably receives the stud 36 secured to support 14 and extending upwardly therefrom. The upper end of the stud 36 is threaded and is adapted to receive the wing nut 38 to maintain slide member 28 in various lateral positions with respect to support 14. As seen in FIG. 3, slide member 28 includes a rearwardly extending portion 40. Gear rack 42 having rearwardly presented teeth 44 is positioned in recessed area 32 of slide member 28 and is secured thereto by screws or the like. The teeth 44 are adapted to engage the teeth of a gear wheel 46 which is rotatably mounted on stud 48 which extends upwardly from support plate 14.

The numeral 50 refers to a slide member which is substantially the mirror image of slide member 28 and which has a gear rack 52 positioned in recessed area 54 and which includes forwardly presented teeth 56 which mesh with the teeth of gear wheel 46. Slide member 50 also has a forwardly extending portion 58, as seen in FIG. 3.

The slide members 28 and 50 serve as the supports for guide members 60 and 62 which are secured to the slide members 28 and 50 at the inner sides of the rearwardly extending portion 40 and the forwardly extending portion 58, respectively. As seen in FIG. 3, the rearward ends of the guide members 60 and 62 have tapered portions 64 and 66, respectively, for a purpose to be described hereinafter.

A threaded bolt 68 is threadably secured to slide member 50, as illustrated in FIG. 3, and a threaded bolt identical to bolt 68 is threadably secured to the outer side of slide member 28. The threaded bolts serve as grips to enable the slide members 28 and 50 to be moved towards one another and moved away from one another. As seen in FIG. 3, the inner surfaces of the guide members 60 and 62 are provided with tapered guide surfaces 70 and 72, respectively, adapted to receive and position the bone graft having a shape other than a cylindrical shape.

The numeral 74 refers to a cutting wheel support which is secured to the support plate 14 rearwardly of the slide members 28 and 50, as illustrated in the drawings. Support 74 rotatably supports a pair of cylindrical cutting wheels or cylinders 76 and 78 which are horizontally spaced-apart from one another and which are vertically disposed. Gear wheels 79 and 80 are positioned on the upper ends of the cutting wheels 76 and 78 for rotation therewith and are in mesh with one another. The cutting wheels 76 and 78 are rotatably mounted by means of the shafts 82 and 84, respectively. Cover 86 is secured to the upper end of the support 74 and has a pair of openings 88 and 90 formed therein which receive the upper ends of the shafts 82 and 84, respectively. As seen in the drawings, the upper end of the shaft 82 extends upwardly from the cover 86. Shaft 82 is secured to the gear wheel 79 and the cutting wheel 76 so that rotation of the shaft 82 by the power means 92, which may be an electric drill, will cause the rotation of gear wheel 79 and cutting wheel 76 which in turn causes the rotation of gear wheel 80 and grinding wheel 78. As seen in the drawings, the cutting wheels 76 and 78 have an hourglass configuration to define a cylindrical opening 94 therebetween. The cutting wheels 76 and 78 are provided with a plurality of radially spaced-apart cutting blades 96 and 98 thereon. As seen in FIG. 3, the lower ends of the cutting wheels 76 and 78 do not have cutting blades thereon, since those lower end portions are received in the recesses 100 and 102 formed in the support 74. Plate 104 is secured to the forward end of support 74 and extends thereacross, as seen in the drawings. As seen in the drawings, the lower end of plate 104 has an inverted V-shaped opening 106 formed therein which limits the upward movement of the bone as it is passing through the cutting wheels.

Figures 2A, 2B:
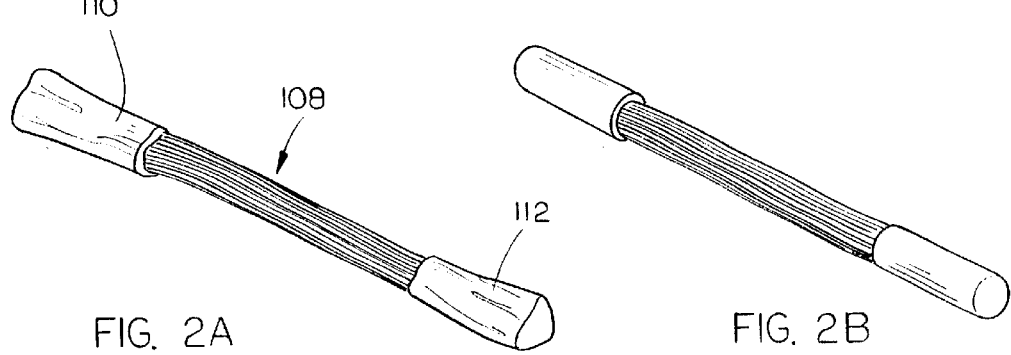
FIG. 2A is a perspective view of the bone plugs prior to being ground.
FIG. 2B is a perspective view illustrating the bone plugs after they have been cut into a cylindrical shape.

FIG. 1 and FIG. 2A illustrate the harvested bone plug which is referred to generally by the reference numeral 108. As seen in the drawings, the harvested bone plug 108 has square or triangular shaped bones 110 and 112 at the opposite ends thereof. An exit support structure 114 is provided rearwardly of the grinding cylinders to maintain the bone plug in a horizontal position.

In use, the wing nut 38 is first loosened so that the slide members 28 and 50 may be moved either outwardly or inwardly to provide the proper spacing between the inclined surfaces 70 and 72 of the guide members 60 and 62, respectively. The movement of the slide members 28 and 50, with respect to one another, is coordinated by the interaction of the gear wheel 46 in engagement with the gear racks 42 and 52 to ensure that the slide members 28 and 50 will be moved inwardly and outwardly the same amount.

Once the guide members 60 and 62 have been properly positioned, the wing nut 38 is tightened to prevent further movement of the slide members 28 and 50. The power means is then attached to the upper end of the shaft 82 and energized so that the gear wheels 76 and 78 are rotated. Cutting wheel 76 is rotated in a clockwise fashion, as viewed in FIG. 3, and cutting wheel 78 is rotated in a counterclockwise direction, as viewed in FIG. 3. End 110 of the harvested bone plug 108 is then positioned between the inclined surfaces 70 and 72 of the guide members 60 and 62, respectively, and is fed rearwardly into engagement with the rotating cutting wheels 76 and 78. The cutting wheels cut the bone on the harvested bone plug to create a cylindrical shape thereto. Once the end 110 has been cylindrically shaped, the bone plug 108 may be withdrawn from the device and the end 112 inserted thereinto.

Thus it can be seen that a novel device has been provided for creating cylindrical bone plugs for patella tendon-tibia grafts which accomplishes at least all of its stated objectives.

I claim:

1. A device for creating cylindrical bone plugs for patella-patellar tendon-tibia grafts, comprising:

a support having forward and rearward ends;

and a bone cutting mechanism on said support for cutting bone plugs, having other than a cylindrical shape, to create cylindrical bone plugs;

said bone cutting mechanism being positioned on said support rearwardly of the forward end thereof and wherein a bone plug guide means is positioned on said support forwardly of said bone cutting mechanism for guiding the bone plugs into engagement with said bone cutting mechanism;

said guide means comprising spaced-apart guide members adapted to have the bone plug movably positioned therebetween.

2. The device of claim 1 wherein said guide means is adjustable.

3. The device of claim 1 wherein the space between said guide members is selectively adjustable.

4. The device of claim 1 wherein each of said guide members has a guide surface or engagement with the bone plug being cut.

5. The device of claim 4 wherein said guide surfaces are inclined to create a truncated, inverted V-shape.

6. The device of claim 4 wherein said guide members are removably secured to said support.

7. A device for creating cylindrical bone plugs for patella-patellar tendon-tibia grafts, comprising:

a support having forward and rearward ends;

and a bone cutting mechanism on said support for cutting bone plugs, having other than a cylindrical shape, to create cylindrical bone plugs;

said bone cutting mechanism comprising a pair of horizontally spaced and vertically disposed cutting wheels which are rotatable about vertical axes.

8. The device of claim 7 wherein one of said cutting wheels is power driven and wherein the other of said cutting wheels is driven by the rotation of said one cutting wheel.

9. The device of claim 8 wherein a gear mechanism interconnects said cutting wheels.

10. The device of claim 7 wherein each of said cutting wheels comprises a cylindrical member having an hourglass configuration.

11. The device of claim 10 wherein each of said cutting wheels have spaced-apart cutting blades provided thereon.

* * * * *